US008278449B2

United States Patent
Khosravi et al.

(10) Patent No.: US 8,278,449 B2
(45) Date of Patent: Oct. 2, 2012

(54) THERMALLY SWITCHABLE RUTHENIUM INITIATORS

(75) Inventors: Ezat Khosravi, Gilesgate Moor (GB); Osama M. Musa, Hillsborough, NJ (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

(21) Appl. No.: 13/211,388

(22) Filed: Aug. 17, 2011

(65) Prior Publication Data

US 2011/0301297 A1 Dec. 8, 2011

Related U.S. Application Data

(63) Continuation of application No. PCT/US2010/024423, filed on Feb. 17, 2010.

(60) Provisional application No. 61/153,372, filed on Feb. 18, 2009.

(51) Int. Cl.
*C07F 15/00* (2006.01)
*C08F 4/80* (2006.01)

(52) U.S. Cl. ............... 546/4; 526/171; 546/2

(58) Field of Classification Search ............ 546/4, 2; 526/171
See application file for complete search history.

(56) References Cited

U.S. PATENT DOCUMENTS

2006/0058476 A1 3/2006 Piccinelli et al.

FOREIGN PATENT DOCUMENTS

WO 9900397 A1 1/1999
WO 2005028402 A2 3/2005

OTHER PUBLICATIONS

Slugove, Christian et al. "Thermally Switchable Olefin Metathesis Initiators," Organometallics, American Chemical Society, 2005, vol. 24, pp. 2255-2258.
Van Der Schaff, Paul A. et al. "Synthesis and reactivity of novel ruthenium carbine catalysts," Journal of Organometallic Chemistry, Elsevier Science S.A., vol. 606, No. 1, Jul. 14, 2000, pp. 65-74.
Jung, Stefan et al. "A Series of Vinylidene-, Vinyl-, Carbene- and Carbyneruthenium(II) Complexes with [Ru(PCy3) 2] and [Ru(PiPr3)2] as Molecular Building Blocks," European Journal of Inorganic Chemistry, Wiley-VCH GmbH & Co. KGaA, vol. 2004, No. 3, Feb. 2004, pp. 469-480.
Grubbs' Catalysts & MacMillan's Organocatalysts. Sigma-Aldrich, vol. 2., 2002 Supplement, Retrieved from http://www.sigmaaldrich.com/chemistry/chemical-synthesis/learning-center/chemfiles/chemfile-2001-2003/vol-2-supplement on Sep. 26, 2011.
Olefin Metathesis, Grubbs Reaction. Organic Chemistry Portal, Retrieved from http://www.organic-chemistry.org/namedreactions/olefin-metathesis on Sep. 27, 2011.
Grubbs Catalyst, 1st generation, 579726. Aldrich, Sigma-Aldrich, Retrieved from http://www.sigmaaldrich.com/catalog/search/ProductDetail/Aldrich/579726 on Jun. 17, 2008.
Grubbs Catalyst, 2nd generation, 569747. Aldrich, Sigma-Aldrich, Retrieved from http://www.sigmaaldrich.com/catalog/search/ProductDetail/ALDRICH/569747 on Jun. 17, 2008.

*Primary Examiner* — Charanjit Aulakh
(74) *Attorney, Agent, or Firm* — Jane E. Gennaro (57) ABSTRACT

This invention relates to ruthenium initiators for the ring-opening metathesis polymerization (ROMP) of cyclic olefins that are inactive at room temperature but activatable at elevated temperature (referred to as ("thermally switchable"). In general, these are compounds of ruthenium metal to which are bonded four or five ligands, in which one ligand is a pyridine ring in which the nitrogen is chelated to the ruthenium, or a five or six membered ring incorporating nitrogen and the ruthenium in which the nitrogen is chelated to the ruthenium.

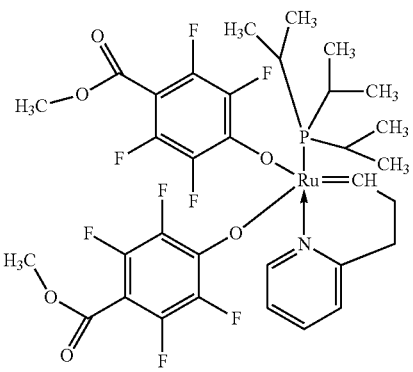

4 Claims, 3 Drawing Sheets

Figure 1: Scheme to introduce functionality into polymers

Figure 2: Structures of Supported Initiators

DS Y1

DS Y2

DS Y3

IMesH$_2$ =

● = resin support

PEG = polyethylene glycol

Py = pyridine

Ph = phenyl

Cy = cyclohexane

Figure 3: Synthesis of DRY11 to DRY13

THERMALLY SWITCHABLE RUTHENIUM INITIATORS

CROSS-REFERENCE TO RELATED APPLICATIONS

This application is a continuation of International Application No. PCT/US2010/024423 filed Feb. 17, 2010, which claims the benefit of U.S. Provisional Application No. 61/153,372 filed Feb. 18, 2009, the contents of both of which are incorporated herein by reference.

BACKGROUND OF THE INVENTION

The polymerization of cyclic monomers in the presence of catalysts containing metals, such as, tungsten, molybdenum, rhenium, and ruthenium, yields linear polymers that retain the carbon-carbon double bonds that were present in the monomer. This polymerization is known as Ring Opening Metathesis Polymerization or ROMP. Successful catalysts for ROMP include the Grubbs' catalysts, benzylidene-bis(tricyclohexylphosphine)-dichlororuthenium and benzylidene[1,3-bis(2,4,6-trimethylphenyl)-2-imidazolidinylidene]dichloro(tricyclohexylphosphine)ruthenium. Other known initiators for ROMP reactions are a nitrogen-containing initiator and a sulfur-containing initiator attributed to the work of Ciba Corporation; and those synthesized by Christian Slugovc. These catalysts, however, can be active at room temperature and are not always the preferred choice for compositions that need to be transported or stored. This creates a need for an efficient catalyst for the polymerization of cyclic olefins, particularly dicyclic olefins, that is thermally switchable, inactive at room temperature, and active at an elevated temperature.

SUMMARY OF THE INVENTION

This invention relates to ruthenium initiators for the ring-opening metathesis polymerization (ROMP) of cyclic olefins that are inactive at room temperature but activatable at elevated temperature (referred to as ("thermally switchable"). In general, these are compounds of ruthenium metal to which are bonded four or five ligands, in which one ligand is a pyridine ring in which the nitrogen is chelated to the ruthenium, or a five or six membered ring incorporating nitrogen and the ruthenium in which the nitrogen is chelated to the ruthenium. The inventors hypothesized that the stronger the chelation, the less activatable the initiator at room temperature, and therefore, the substitution of appropriate ligands onto the ruthenium to strengthen the chelation would provide a room temperature stable initiator. The ruthenium initiators of this invention are prepared by substituting onto known initiators (such as the Grubbs or Slogovc initiators) ligands having electron donating or electron withdrawing properties.

Figure 1:
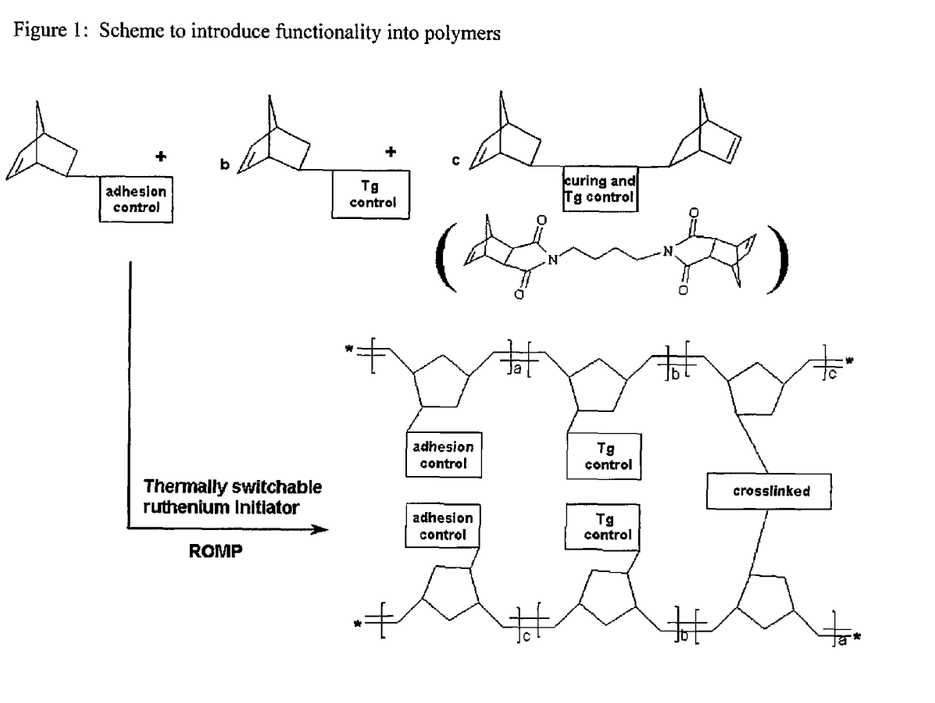
FIG. 1 depicts a scheme to introduce functionality into polymers.

The impetus for using ROMP reactions on cyclic olefins is to preserve the carbon to carbon double bonds from the olefins into the resultant polymers. When the cyclic olefins are further functionalized with additional substituents (other than the carbon to carbon double bond), these additional substituents are also preserved in the resultant polymers, giving the formulating scientist a wide variety of options for designing molecules to meet particular end applications. The reaction scheme for making use of ROMP to produce such molecules is shown in FIG. 1.

In a further embodiment, this invention is a curable composition comprising one or more dicyclic olefins and a ruthenium initiator, in which the ruthenium initiator has one of the structures described in this specification.

In a further embodiment, this invention is a one stage process for the ROMP of dicyclic olefins in the presence of one of the ruthenium initiators shown above.

In a further embodiment, this invention is a polymer resulting from the ROMP of dicyclic olefins in which the dicyclic olefins contain functionality additional to the carbon to carbon double bonds, and in which the resultant polymer contains carbon to carbon double bonds and the additional functionality.

DETAILED DESCRIPTION OF THE INVENTION

Cyclic Olefins

Suitable cyclic olefins are either synthesized or chosen from commercial sources. The base structure of suitable cyclic olefins include:

and which base structures will contain substituents that impart additional functionality to the resultant polymer. For example, a substituent can be a moiety that will control the glass transition temperature or modify the adhesion of the resultant polymer. Useful substituents include alkyl and aryl groups, including those with heteroatoms, and other functional groups that will be non-reactive with the ruthenium initiators of this invention, such as, epoxy or oxetane groups.

Ligands and Syntheses

As used in this specification and the claims, ligands refers to compounds that both can be or have been covalently bonded to the ruthenium metal.

LIGAND L5: same as L6 and L7 except that aniline is used instead of 4-methoxyaniline or 4-methylaniline in its preparation.

LIGAND L6

Synthesis: Ligand L6 was prepared from 2-vinylbenzaldehyde (2-VBA), according to the following reaction procedure: 0.00226 mol (418 mg) of 2-bromobenzaldehyde was mixed with 0.00226 mol (545 mg) vinylboronic anhydride pyridine-complex, 0.113 mmol (5 mol %, 0.122 g) tetrakis-triphenyl-phosphine palladium and 0.00226 mol (312 mg) potassium carbonate in a 2-neck flask under nitrogen (all were mixed in the glovebox). The flask was equipped with a condenser and a stirrer bar. A mixture of dimethoxyethane (DME) and water in ratio 1/1 was degassed for 15 minutes by bubbling $N_2$ gas through it, after which this mixture was added to the reaction flask. The reaction mixture was heated up to 100° C. for 17 hours. The reaction was stopped and dichloromethane (DCM) was added for extraction. The DCM extracts were dried over $MgSO_4$ overnight, after which the $MgSO_4$ was filtered off and DCM evaporated. The remaining mixture of solid and brown viscous liquid was again dissolved in a minimum amount of DCM and put in the freezer for one day to precipitate out any impurities coming from the palladium and borone complexes. After freezing, yellow precipitate was observed and filtered off. DCM was evaporated giving a brown viscous liquid, determined to be the pure 2-VBA by proton NMR, in a yield of 80%.

The 2-VBA product (0.004 mol, 0.5 g) was mixed with 0.004 mol (0.47 g) 4-methoxyaniline and 6 ml of dry ethanol in a 2-neck flask equipped with condenser and a stirrer bar under nitrogen. The mixture was heated to 100° C. for five hours. After the reaction was stopped, the ethanol was evaporated resulting in a light brown viscous liquid, which was the pure product. NMR showed no remaining starting materials or side products.

LIGAND L7

Synthesis: The same 2-VBA product used for L6, (0.004 mol, 0.5 g), was mixed with 0.004 mol (0.43 g) 4-methylaniline and 6 ml of dry ethanol in a 2-neck flask equipped with condenser and a stirrer bar under nitrogen. The mixture was heated to 100° C. for five hours. After the reaction was stopped, the ethanol was evaporated resulting in a light brown viscous liquid, which was the pure product. NMR showed no remaining starting materials or side products.

LIGAND L8

Synthesis: 4-Nitroaniline (0.00152 mol, 0.22 g) was mixed with 1.1 ml of triethylamine and 10 ml dry DCM in a 2-neck flask equipped with condenser and a stirrer bar under nitrogen. The mixture was cooled to −50° C. (dry ice/acetone bath). Subsequently 0.6 ml 1M solution of $TiCl_4$ in DCM was added slowly under an inert atmosphere of nitrogen, followed by slow addition of the product obtained from step 1,2-VBA (0.00152 mol, 0.2 g). The cooling bath was removed and the reaction was stirred at room temperature for 20 hours. After removing the solvent, 10 ml diethylether were added to the resulting solid. The resulting suspension was stirred vigorously for one hour. The solid was then filtered off and the ether was evaporated from the remaining liquid, giving a dark yellow solid determined to be the pure ligand by NMR.

LIGAND L9

Synthesis: To a solution of 2,3,5,6-tetrafluoro-4-hydroxybenzoic acid hydrate (5.2 g) in methanol (400 ml) was added concentrated sulphuric acid (98%) (2 ml). The solution was heated to reflux and kept overnight. TLC (thin layer chromatography) was used to monitor the reaction. After the complete conversion, methanol was removed; then water (100 ml) was added to the residual. Dichloromethane was used to precipitate the methyl 2,3,5,6-tetrafluoro-4-hydroxybenzoate extract from the aqueous solution. The extract was dried by anhydrous magnesium sulphate and concentrated to give a white solid (5.01 g), which was used without further purification, or recrystallized in toluene.

To a solution of methyl 2,3,5,6-tetrafluoro-4-hydroxybenzoate (1.02 g, 4.55 mmol) in anhydrous tetrahydrofuran (10 ml) was added a solution of thallium ethoxide (1.19 g, 4.78 mmol, 1.05 eq) in anhydrous tetrahydrofuran (5 ml). A white solid precipitated out and the precipitate suspension was stirred for further three hours. The white solid product was collected, washed with anhydrous tetrahydrofuran, and then dried under reduced pressure. It was used without further purification.

LIGAND L10

Synthesis: Prepared according to a literature procedure [P. A. Van der Schaaf et al: *Journal of Organometallic Chemistry* 606 (2000) 65-74]. A total of 100 ml butyllithium (2.5 M sol. in hexane, 0.25 mol) was added dropwise over a period of one hour to a cooled solution of 2-methyl-pyridine (23.3 g, 0.25 mol) in 80 ml THF (tetrahydrofuran) of 0° C. The reaction mixture was a clear orange color. The temperature of the reaction mixture was kept at 0-5° C. during the addition of the butyllithium solution. After addition, the reaction mixture was stirred for an additional 30 minutes at 0° C. and kept at 0° C. as it was added dropwise over a period of 30 minutes to a cooled solution of allyl chloride (19.1 g, 0.25 mol) in 320 ml THF. During the addition of the organolithium intermediate, the temperature was kept at 0-5° C. After addition, the final reaction mixture was stirred for an additional 30 minutes. A total of 20 ml of isopropanol was added (to quench the remaining organolithium species) keeping the reaction mixture between 0 and 5° C. The reaction mixture, a yellow suspension, was warmed to room temperature and 80 ml of a saturated sodium chloride solution in water were added. The resulting suspension was filtered over Celite, and the Celite was extracted with ether (3×100 ml). The organic phase was separated from the combined reaction mixture with the ethereal washings and dried over magnesium sulfate. The organic phase was concentrated under reduced pressure giving the crude product. The product was purified by distillation (42-50° C.), and obtained as a colorless liquid in 74% yield (23.7 g).

LIGAND L11 in which R is H, OCH$_3$, or NO$_2$ (Schiff base ligands).

2-Amino-phenethylalcohol (5.5 g, 40 mmol) and potassium hydroxide (2.25 g, 40 mmol) were combined in a distillation apparatus, then heated to 180° C. under vacuum. A clear, colourless oil (3.5 g) was obtained over four hours at 147-148° C. at 3.5 mmHg in a 74% yield. 2-Vinyl-phenylamine and the corresponding aldehyde (1.1 eq) (unsubstituted, or substituted with OCH$_3$, or NO$_2$ on the ring) were mixed in absolute ethanol. The solution was heated to reflux and kept for overnight. After removal of solvent under reduced pressure, the crude product was obtained and used without further purification.

Ruthenium Initiators and Syntheses

The ruthenium initiators of this invention and their syntheses are reported here. In some instances other initiators were prepared and used in the synthesis of the inventive initiators, and these are identified by Roman numeral in a later section of this specification. All reactions involving metal complexes were conducted in oven-dried glassware under a nitrogen atmosphere using standard Schlenk techniques and anhydrous solvents. All commercial reagents were used as received. $^1$H and $^{13}$C NMR spectra were recorded on Varian Mercury 300 Spectrometer (at 300 and 75 MHz, respectively) and the chemical shifts are reported in ppm relative to tetramethylsilane (δ0.0).

Initiators DN1-DN3 were fully characterized by $^1$H and $^{13}$C NMR spectroscopy and their structures were confirmed by X-ray crystallography, Initiator DY1

Synthesis: Thallium salt of methyl 2,3,5,6-tetrafluoro-4-hydroxybenzoate (9) (2 eq) and ruthenium initiator (III) (1 eq) was mixed in dichloromethane in a glovebox. The resulting mixture was kept to stir overnight at ambient temperature. After the removal of the solid, the filtrate was reduced to dryness. Precipitation from dichloromethane-hexane afforded a brown powder.

Initiator DY2

Synthesis: Thallium salt of methyl 2,3,5,6-tetrafluoro-4-hydroxybenzoate (9) (2 eq) and initiator VIII (1 eq) were mixed in dichloromethane in a glovebox. The resulting mixture was kept to stir overnight at ambient temperature. After the removal of the solid, the filtrate was reduced to dryness and washed with dichloromethane-hexane (1:5 v/v) to afford a green powder.

Initiator DY3

Synthesis: Thallium salt of methyl 2,3,5,6-tetrafluoro-4-hydroxybenzoate (9) (2 eq.) and initiator VII (1 eq) was mixed in dichloromethane in a glove box. The resulting mixture was kept to stir overnight at ambient temperature. After the removal of the solid, the filtrate was reduced to dryness. The solid was washed with dichloromethane-hexane (1:5 v/v) to afford a brown powder.

Initiator DY4

Synthesis: Thallium salt of methyl 2,3,5,6-tetrafluoro-4-hydroxybenzoate (2 eq) and initiator IX (1 eq) was mixed in dichloromethane in a glove box. The resulting mixture was kept to stir overnight at ambient temperature. After the removal of the solid, the filtrate was reduced to dryness. The solid was washed with dichloromethane-hexane (1:5 v/v) to afford a green powder.

Initiator DY5

Synthesis: Silver meththanesulfonate (2 eq) and initiator I (1 eq) was mixed in anhydrous tetrahydrofuran in a glovebox. The resulting mixture was kept to stir overnight at ambient temperature. After the removal of the solid, the filtrate was reduced to dryness to afford a dark green powder.

The initiator DY5 bear two MeO$_2$SO— ligands. Ruthenium Grubbs second generation (II), commercially available (Aldrich), is modified with pyridine to prepare pyridine modified ruthenium second generation (VIII). The reaction of VIII with the MeSO$_3$Ag gives DY5. Initiator DY5 was characterised by $^1$HNMR and $^{13}$CNMR.

The DSC studies of ROMP of 2-EHNB monomer with initiator DY5 shows a sharp exotherm peak with the maximum of 87° C. and ΔH of 153 J/g. The reaction onset temperature was 73° C. and the polymerisation was over by 110° C. The DSC studies of ROMP of HNB monomer with initiator DY5 shows a sharp exotherm peak with the maximum of 87° C. and ΔH of 153 J/g. The reaction onset temperature was 75° C. and the polymerisation was over by 110° C. Initiator DY5 appears to give same results for both 2-EHNB and HNB monomers.

Initiator DY6

Synthesis: Ligand L11 (1.5 eq) and initiator I (1 eq) were mixed in dichloromethane in a glove box. The resulting mixture was kept to stir overnight at ambient temperature. After the removal of the volatiles, the solid was washed with hexane or a mixture of dichloromethane and hexane (1:5 v/v) to afford a powder.

Initiator DY7

Synthesis: Ligand L11 in which R is OCH$_3$ (1.5 eq.) and initiator I (1 eq.) were mixed in dichloromethane in a glove box. The resulting mixture was kept to stir overnight at ambient temperature. After removal of the volatiles, the solid was washed with hexane or a mixture of dichloromethane and hexane (1:5 v/v) to afford the product as a powder.

Initiator DY8

Synthesis: Ligand L11 in which R is NO$_2$ (1.5 eq.) and initiator III (1 eq.) were mixed in dichloromethane in a glove box. The resulting mixture was kept to stir overnight at ambient temperature. After removal of the volatiles, the solid was washed with hexane or a mixture of dichloromethane and hexane (1:5 v/v) to afford the product as a powder.

Initiator DY9

Synthesis: Ligand L11 in which R is NO$_2$ (1.5 eq.) and initiator I (1 eq.) were mixed in dichloromethane in a glove box. The resulting mixture was kept to stir overnight at ambient temperature. After removal of the volatiles, the solid was washed with hexane or a mixture of dichloromethane and hexane (1:5 v/v) to afford the product as a powder.

Initiator DY10

Synthesis: Ligand L11 in which R is H (1.5 eq.) and initiator I (1 eq.) were mixed in dichloromethane in a glove box. The resulting mixture was kept to stir overnight at ambient temperature. After removal of the volatiles, the solid was washed with hexane or a mixture of dichloromethane and hexane (1:5 v/v) to afford the product as a powder.

Initiator DN1

Synthesis: Initiator I (0.1 g, 0.000137 mol) was dissolved in 2 ml dry dichloromethane (DCM) and mixed with 0.000206 mol (1.5 eq.) of ligand L6 (49 mg) dissolved in 2 ml dry DCM. The mixture was stirred overnight, then DCM evaporated under reduced pressure. The solid residue was dissolved again in a minimum amount of DCM and precipitated in cold dry hexane (10 times the amount of DCM used). The precipitated solid was filtered off and washed one more time with cold dry hexane. The product was dried under vacuum at room temperature and yielded>90%.

Initiator DN2

Synthesis: Initiator I (0.1 g, 0.000137 mol) was dissolved in 2 ml dry dichloromethane (DCM) and mixed with 0.000206 mol (1.5 eq.) of ligand L7 (46 mg) dissolved in 2 ml dry DCM. The mixture was stirred overnight. Then the DCM was evaporated under reduced pressure. The solid residue was dissolved again in a minimum amount of DCM and precipitated in cold dry hexane (10 times the amount of DCM used). The precipitated solid was filtered off and washed one more time with cold dry hexane. The product was dried under vacuum at room temperature and yielded>90%.

Initiator DN3

Synthesis: Initiator I (0.1 g, 0.000137 mol) was dissolved in 2 ml dry dichloromethane (DCM) and mixed with 0.000206 mol (1.5 eq.) of ligand L8 (52 mg) dissolved in 2 ml dry DCM. The mixture was stirred overnight, then DCM evaporated under reduced pressure. The solid residue was dissolved again in a minimum amount of DCM and precipitated in cold dry hexane (10 times the amount of DCM used). The precipitated solid was filtered off and washed one more time with cold dry hexane. The product was dried under vacuum at room temperature and yielded>90%.

Initiator S5

Synthesis: Prepared the same as DN1 and DN2 using ligand L5.

DSY1

Figure 2:
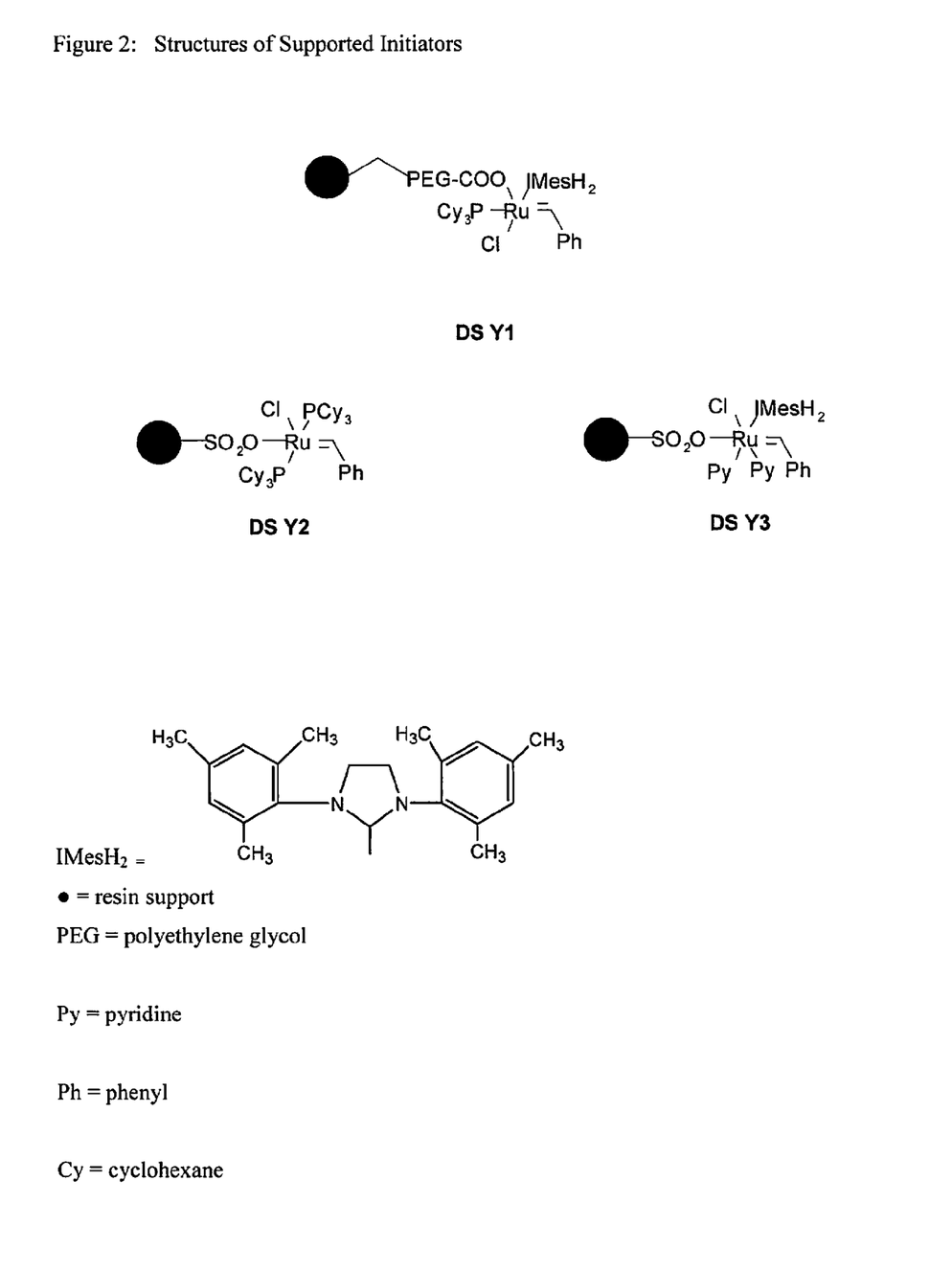
FIG. 2 depicts the structures of supported initiators.
Figure 3:
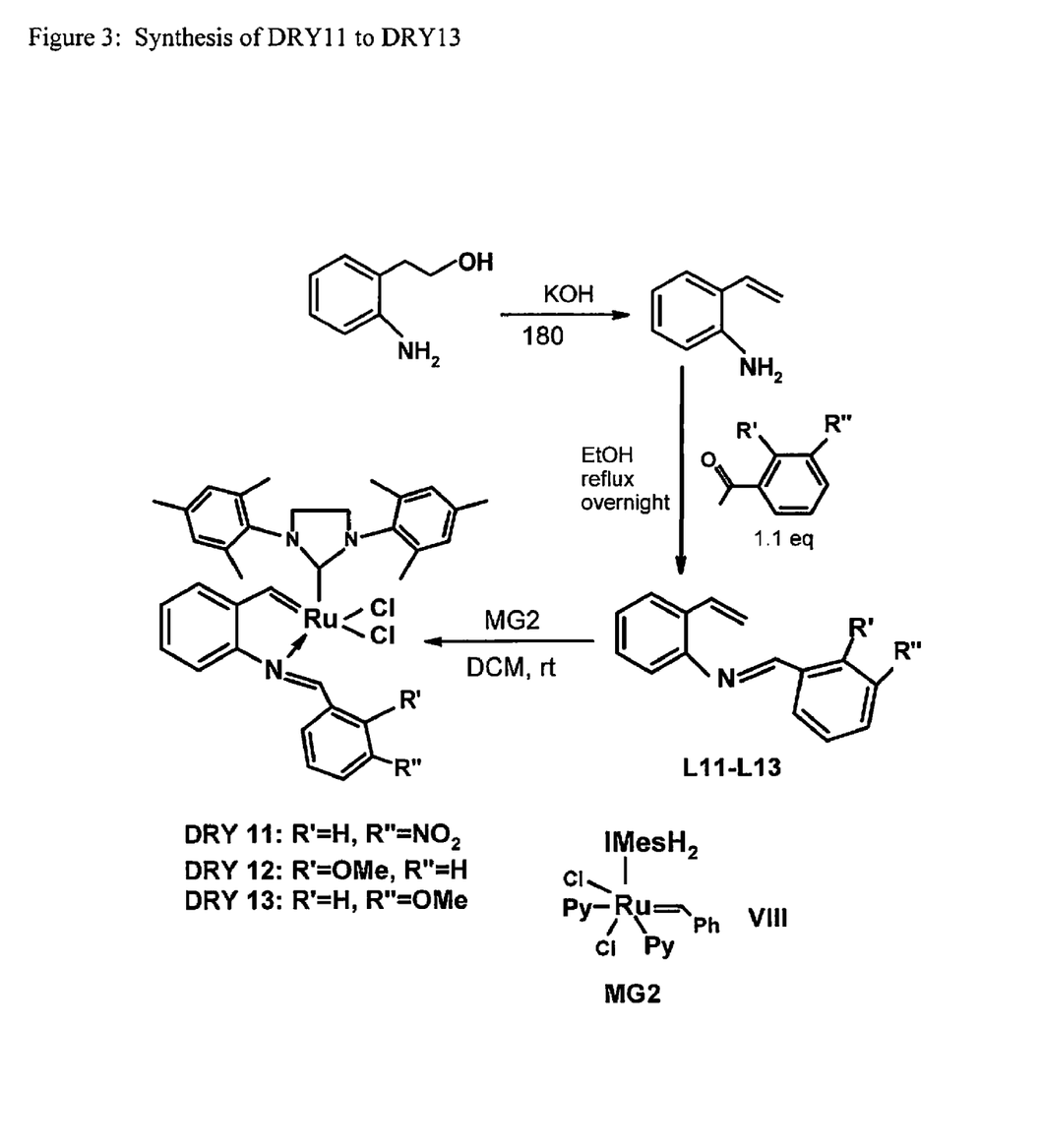
FIG. 3 depicts the synthesis of DRY11 to DRY13.

See FIG. 2 for structure.

Synthesis: NovaSyn TG carboxy resin (Merck Bioscience, 0.26 mmol/g) (0.5 g) was eluted by using NaOH (1M, 10 eq) and water until pH=7. The resin was treated with silver nitrate (1M, 4 eq) and water until no silver ion in the eluate. The resin was washed with methanol and dried under vacuum to give a silver loading (0.1 mmol/g) by silver analysis. The resin was treated with initiator II (2.5 eq) in THF in a glove box for overnight at room temperature. The resin was washed by THF until colourless liquid found. The resin was dried and gave a loading of Ru initiator (0.05 mmol/g phosphorus analysis and Ru analysis (Ion Beam Analysis)).

DSY2 and DSY3

See FIG. 2 for structures.

Synthesis: Sulfonic acid resin (Amberlite, 3.4 mmol/g) (0.5 g) was eluted by using NaOH (1M, 10 eq) and water until pH=7. The resin was treated with silver nitrate (1M, 4 eq) and water until no silver ion in the eluate. The resin was washed with methanol and dried under vacuum to give a silver loading (2.24 mmol/g) by silver analysis. The resin was treated with Ru initiator I (2.5 eq) or VIII in THF in a glove box for overnight at room temperature. The resin was washed by THF until colourless liquid found. The resin was dried and gave supported initiators DSY2 and DSY3 respectively. Silver analysis shows that silver content was lower than in the starting materials.

Other Initiators

Initiator I: Grubbs first generation initiator available from Aldrich

Initiator II. Grubbs second generation initiator available from Aldrich

Initiator III
Commercially available from Ciba Corporation.

Initiator V
Slugovc initiator

Initiator VI

Initiator VII

Method A: In a glove box, initiator III (0.1 mmol) and tricyclohexylphosphine (10 eq) were mixed into dichloromethane (5 ml). The reaction was kept at room temperature for overnight. The volatiles were removed under reduced pressure and the residue triturated with hexanes. The solid was collected, washed with hexanes (3×10 ml) and dried under reduced pressure to give initiator VII (0.057 mmol) as a pale green solid upon drying. Yield: 57%.

Method B: In a glove box, initiator I (0.1 mmol) and Ligand (10) (10 eq) were mixed into dichloromethane (5 ml) and then the reaction allowed to stir at room temperature for overnight. The volatiles were removed under reduced pressure and the residue triturated with hexanes. The solid was collected, washed with hexanes (3×5 ml) and dried under reduced pressure to give initiator VII (0.065 mmol) as a pale green solid upon drying. Yield: 65%.

Initiator VIII

Initiator II (1 g) was dissolved in 4 ml of DCM. Excess pyridine (2 ml) was added to the solution and the mixture was stirred at room temperature in a glovebox for two hours. After that, the DCM was evaporated under reduced pressure, the residue was dissolved again in a minimum amount of DCM and precipitated in 10 times higher volume of cold hexane. The obtained solid was filtered off, washed again with cold hexane, and dried under reduced pressure.

Initiator IX

Method A: In a glove box, initiator II (0.1 mmol) and ligand L10 (10 eq) were mixed into dichloromethane (5 ml). The reaction was heated to reflux and kept for five hours. The volatiles were removed under vacuum and the residue triturated with hexanes. The solid was collected, washed with hexanes (3×10 ml) and dried under vacuum to give initiator IX (0.061 mmol) as a pale green solid upon drying. Yield: 61%.

Method B: In a glove box, initiator VIII (0.1 mmol) and ligand L10 (10 eq) were mixed into dichloromethane (5 ml) and then the reaction allowed to stir at room temperature for overnight. The volatiles were removed under vacuum and the residue triturated with hexanes. The solid was collected, washed with hexanes (3×5 ml) and dried under vacuum to give initiator IX (0.069 mmol) as a pale green solid upon drying. Yield: 69%.

Romp Activity of Initiators DY1-DY5

The ROMP activity and hence thermal switchability were investigated by DSC and NMR.

BY DSC STUDIES. A heating rate of 3° C. per minute and a heating range of 20°-140° C. were used for all experiments. The conversions were calculated from $^1$H NMR spectra of the polymerization mixtures in the DSC pans after the DSC measurements were complete. The results are summarized in the following table.

ROMP of hexyl imidonorbornene (HNB) monomer using DY1 initiator exhibited the exotherm maximum at around 100° C.

ROMP of 2-ethylhexyl imidonorbornene (2-EHNB) monomer using DY1 showed the exotherm maximum at around 113° C.

ROMP of decyl imidonorbornene (DecNB) monomer using DY1 exhibited the exotherm peak at around 108° C.

ROMP of 2-EHNB monomer with initiator DY5 exhibited a sharp exotherm peak with the maximum of 87° C. and ΔH of 153 J/g. The reaction onset temperature was 73° C. and the polymerization was over by 110° C.

ROMP of HNB monomer with initiator DY5 exhibited a sharp exotherm peak with the maximum of 87° C. and ΔH of 153 J/g. The reaction onset temperature was 75° C. and the polymerisation was over by 110° C.

Initiator DY5 appears to give the same results for both 2-EHNB and HNB monomers and in both ROMP reactions a secondary exotherm appears with the maxima of 125° C.

By $^1$HNMR Studies (DY1-DY4)

ROMP reactions were carried out in a solution with CDCl$_3$ as solvent and were followed by $^1$H NMR in order to investigate the conversion of each monomer after 24 hours at room temperature and after 24 hours at 55° C.

The $^1$H NMR spectra of the reaction mixture for the ROMP of hexyl imidonorbornene (HNB) monomer using DY1 showed conversion of monomer to polymer of 7% after 24 hours at room temperature and 89% after 20 hours at 55° C. The conversion level using initiator I under the same conditions is 99% after 24 hours at room temperature.

The $^1$H NMR spectra of the reaction mixture for the ROMP of decyl imidonorbornene (DecNB) monomer using DY1 showed conversion of monomer to polymer of 9% after 24 hours at room temperature and 68% after 20 hours at 55° C. The conversion using initiator I under the same conditions is 99% after 24 hours at room temperature.

The $^1$H NMR spectra of the reaction mixture for the ROMP of 2-ethylhexyl imidonorbornene (2-EHNB) monomer using DY1 showed conversion of monomer to polymer of 7% after 24 hours at room temperature and 68% after 20 hours at 55° C. The conversion using initiator I under the same conditions is 99% after 24 hours at room temperature.

The $^1$H NMR spectra of the reaction mixture for the ROMP of cyclohexyl imidonorbornene (CyNB) monomer using DY1 showed conversion of monomer to polymer of 7% after 24 hours at room temperature and 78% after 20 hours at 55° C. The conversion using initiator I under the same conditions is 90% after 24 hours at room temperature.

The $^1$H NMR spectra of the reaction mixture for the ROMP of phenyl imidonorbornene (PhNB) monomer using DY1 showed conversion of monomer to polymer of 9% after 24 hours at room temperature and 79% after 20 hours at 55° C. The conversion using initiator I under the same conditions is 100% after 24 hours at room temperature.

| INITIATOR | DY1 % CONV. | | DY3 % CONV. | | DY4 % CONV. | INITIATOR I % CONV. |
|---|---|---|---|---|---|---|
| MONOMER | RT 24 hr | 55° C. 20 hr | RT 24 hr | 55° C. 24 hr | RT 18 hr | RT 24 hr |
| HNB | 7 | 89 | 10 | 20 | 99 | 99 |
| DecNB | 9 | 68 | — | — | — | 99 |
| 2EHNB | 7 | 68 | — | — | — | 99 |
| CyNB | 7 | 78 | — | — | — | 90 |
| PhNB | 9 | 79 | — | — | — | 100 |
| ThiazNB | 0 | 0 | — | — | — | 10 |

The $^1$H NMR spectra of the reaction mixture for the ROMP of thiazolyl imidonorbornene (ThiazNB) monomer using DY1 showed no detectable conversion of monomer to polymer after 24 hours at room temperature nor after 20 hours at 55° C. One explanation is that for the ROMP of this monomer higher temperature than 55° C. may be required. The conversion using initiator I under the same conditions is 10% after 24 hours at room temperature.

The $^1$H NMR spectra of the reaction mixture for the ROMP of hexyl imidonorbornene (HNB) monomer using DY3 showed conversion of monomer to polymer of 10% after 24 hours at room temperature and 20% after 24 hours at 55° C.

The $^1$HNMR spectra of the reacting mixture for the ROMP of hexyl imidonorbornene (HNB) monomer using DY4 showed conversion of monomer to polymer of 99% after 18 hours at room temperature.

The results are summarized in the following table.

| INITIATOR | DY1 % CONV. | | DY3 % CONV. | | DY4 % CONV. | INITIATOR I % CONV. |
|---|---|---|---|---|---|---|
| MONOMER | RT 24 hr | 55° C. 20 hr | RT 24 hr | 55° C. 24 hr | RT 18 hr | RT 24 hr |
| HNB | 7 | 89 | 10 | 20 | 99 | 99 |
| DecNB | 9 | 68 | — | — | — | 99 |
| 2EHNB | 7 | 68 | — | — | — | 99 |
| CyNB | 7 | 78 | — | — | — | 90 |
| PhNB | 9 | 79 | — | — | — | 100 |
| ThiazNB | 0 | 0 | — | — | — | 10 |

The results demonstrate that DY1 initiator is inactive at room temperature giving conversion less than 10% after 24 hours. The initiator becomes active at elevated temperature; showing exotherm maximum at 100-113° C. in DSC depending on the nature of the monomer.

ROMP Activity of Initiators DN1-DN3

BY $^1$HNMR STUDIES. All initiators were tested for ROMP using hexyl imidonorbornene (HNB) monomer in solution at room temperature. The reaction was followed by comparing the integration of the peak of the monomer at 6.3 ppm and polymer at 5.4-5.8 ppm to establish the conversion of monomer to polymer.

DN1 initiator gave monomer to polymer conversion of only 9% after 24 h at room temperature and 23% after 92 hours. After heating the reaction at 55° C. for 24 hours, the conversion increased to 40%.

DN2 initiator gave monomer to polymer conversion of only 29% after 24 hours and 97% after 92 hours at room temperature. Because of the high conversion after 48 hours, it was not necessary to heat this reaction at 55° C.

DN3 initiator gave monomer to polymer conversion of 20% after 24 hours at room temperature and it remained unchanged after 48 hours. After heating the reaction at 55° C. for 24 hours, the conversion increased to 40%. The results of $^1$H NMR studies of ROMP of HNB monomer using initiators DN1, DN2, DN3 and Initiator IV are summarized in the following table. The results indicate the lowest monomer to polymer conversion for DN 1 after 24 hours and 48 hours. The monomer to polymer conversion for DN2 and DN3 are higher than DN1 but lower for both in comparison with Initiator 4.

| Reaction time | DN1 % Conversion | DN2 % Conversion | DN3 % Conversion | Control Initiator IV % Conversion |
|---|---|---|---|---|
| 10 min (RT) | 0 | 0 | 0 | 0 |
| 24 h (RT) | 9 | 29 | 20 | 56 |
| 48 h (RT) | 19 | 72 | 20 | 76 |
| 92 h (RT) | 23 | 97 | — | 98 |
| 24 h (55° C.) | 40 | — | 40 | — |

By DSC Studies
Using Hexyl Imidonorbornene (HNB) Monomer

DSC investigations of the course of ROMP of HNB monomer with initiators DN1, DN2, DN3 were performed. All samples for DSC were prepared by dissolving the initiator in a minimum amount of chloroform, mixing it with the monomer, removing the solvent under reduced pressure and placing the sample in the DSC pan. The results of the DSC studies are summarized in the following table.

| | Initiator | | | | | | | | | | |
|---|---|---|---|---|---|---|---|---|---|---|---|
| | DN1 | | | DN2 | | | DN3 | | | Initiator IV | | |
| | start | max | end | start | max | end | start | max | end | start | max | end |
| Exotherm Temps ° C. | 78 | 127 | 185 | 66 | 83 | 130 | 95 | 130 | 260 | 71 | 91 | 135 |
| ΔH (J/g) | | 106 | | | 21 | | | 144 | | | 26 | |

The exotherm peaks' maxima for DN3 (with electron withdrawing group EWG) and DN1 (with electron donating group EDG) are the same, but the peak span is broader for DN3 and it ends at higher temperature. The ΔH for DN3 (with EWG) is larger than that for DN1 (with EDG) and both are substantially larger than that for DN2 (with methyl substitution in para position) and initiator IV, (with no substitution in para position). These results indicate that for the ROMP of HNB monomer, the incorporation of either EDG or EWG in a para position of the benzene ring of the catalyst has no effect on the exotherm peak maximum, but it does greatly influence the ΔH as it was predicted.

Using 2-ethylhexyl imidonorbornene (2-EHNB) monomer

DSC investigations of the course of ROMP reactions using 2-EHNB monomer and initiators DN1, DN2, and DN3 were performed. All samples for DSC were prepared by dissolving the initiator in a minimum amount of chloroform, mixing it with the monomer, removing the solvent under reduced pressure and placing the sample in the DSC pan. The results are summarized in the following table.

| | Initiator | | | | | | | | | | |
|---|---|---|---|---|---|---|---|---|---|---|---|
| | DN1 | | | DN2 | | | DN3 | | | Initiator IV | | |
| | start | max | end | start | max | end | start | max | end | start | max | end |
| Exotherm Temps ° C. | 60 | 119 | 175 | 50 | 79 | 100 | 30 | 70 | 100 | 71 | 91 | 135 |
| ΔH (J/g) | | 159 | | | 18 | | | 104 | | | 26 | |

The peak span (start-end) and exotherm peaks' maxima were found to be close for DN2 and DN3. The peak span and exotherm peak maximum for DN1 were found to be higher than those for DN2 and DN3. The exotherm peaks' maxima for DN3 (with EWG) is lower than DN1 (with EDG) and DN2 (with methyl group in para position of the benzene ring), which it is as predicted. The ΔH for DN1 and DN3 are more than that of DN2 (with methyl substitution in para position). The results indicate that for the ROMP of 2-EHNB monomer the incorporation of EDG and EWG in para position of the benzene ring of the catalyst has the predicted effect on the exotherm peak maximum.

Using a Mixture of Mono- and Di-Functional Imidonorbornene Monomers

DSC investigation of the ROMP behaviour of DN1 and initiator IV with HNB and 5% of the di-functional monomer (crosslinking agent) N-Butyl dinorbornene (BDNB) were also performed. As BDNB is a solid compound, it was dissolved together with the initiator in a minimum amount of solvent, mixed with the liquid monomer, then the solvent was removed under vacuum and the mixture placed in the DSC pan. The results of the DSC studies are summarized in the following table.

| | Initiator | | | | | |
|---|---|---|---|---|---|---|
| | DN1 | | | Control Initiator IV | | |
| | start | maximum | end | start | maximum | end |
| Exotherm temperatures (° C.) | 60 | 124.7 | 220 | 60 | 86.5 | 140 |
| ΔH (J/g) | | 94.8 | | | 60.8 | |

The exotherm peak span for DN1 was found to be broader than for initiator IV. The peak maximum and ΔH for DN1 (with EDG) was higher than for initiator IV (with no substitution).

2-Aminostyrene was obtained by the dehydration of 2-aminophenethyl alcohol in a 74% yield. The Schiff Base ligands (11) were obtained by the reaction of 2-aminostyrene with the corresponding aldehydes. These ligands (11) were used without further purification. Durham initiators DY6-DY10 initiators were obtained by the reaction of Grubbs first or modified second generation initiators in dichloromethane.

ROMP Activity of Initiators DY6-D10

By $^1$HNMR STUDIES: Initiators DY6-D10 were screened for their activities in ROMP of cyclohexyl imidonorbornene (CyNB) monomer. DY6 gave conversion of monomer to polymer of 96% after 24 hours at room temperature. DY7 gave a conversion of monomer to polymer of 42% after 48 hours at room temperature. DY8 gave a conversion of monomer to polymer of 97% after 24 hours at room temperature. DY9 gave a conversion of monomer to polymer of 5% after 24 hours at room temperature. DY10 is not active at all and only gave a conversion of monomer to polymer of <5% after 24 hours at room temperature.

The results are summarized in the following table.

| Reaction Time (h) | DY6 % Conv. | DY7 % Conv. | DY8 % Conv. | DY9 % Conv. | DY10 % Conv. |
|---|---|---|---|---|---|
| 1 | 48 | 7 | 25 | 2 | 0 |
| 3 | | | | | |
| 4 | | 17 | 75 | | 0 |
| 5 | | | | 4 | |
| 8 | | | 90 | | |
| 12 | 87 | | | | |
| 24 | 96 | 39 | 97 | 5 | 5 |
| 48 | | 42 | | | |

The initiator DY6 is active at room temperature and gives a monomer to polymer conversion of 48% after three hours at room temperature. The initiator DY7 is less active than DY6 and it gives a monomer to polymer conversion of 17% in the same timescale. The initiator DY8 is more active than both DY6 and DY7 as it gives a monomer to polymer conversion of 75% after 4 hours at room temperature. Initiators DY9 and DY10 are both inactive at room temperature as they both give a monomer to polymer conversion of about 5% after 24 hours.

By DSC STUDIES. ROMP of 2-ethylhexyl imidonorbornene (2-EHNB) (liquid monomer) using initiators DY6-DY8 initiators were investigated by DSC. For initiators DY6 and DY8, ROMP started at around 80° C. and the exotherm maxima were observed at around 100° C. For initiator DY7, ROMP started at 130° C. and the exotherm maximum was at around 150° C. DY6 and DY8 gave the largest ΔH (175-189 J/g) in comparison with DY7 (124 J/g).

Initiators DY6 and DY8 posses IMesH2 ligand but have Schiff bases containing EDG (OMe) and EWD (NO$_2$) respectively. The fact that initiators DY6 and DY8 show similar characteristics indicate that the presence of EDG or EWD in para position of the benzene ring has no real effect on the ROMP of 2-EHNB monomer. The initiator DY7 contains PCy$_3$ ligand and Schiff base with EDG (OMe). The initiators containing PCy$_3$ are generally less reactive than H$_2$IMes containing initiators and therefore DY7 required higher temperature for its activation.

The results are summarized in the following table.

|  | Initiator | | | | | | | | |
| --- | --- | --- | --- | --- | --- | --- | --- | --- | --- |
|  | DY6 | | | DY7 | | | DY8 | | |
|  | start | max. | End | start | max. | end | start | max. | end |
| Exotherm temp. (° C.) | 81 | 103 | 145 | 130 | 149 | 190 | 78 | 102 | 145 |
| ΔH (J/g) |  | 175 |  |  | 124 |  |  | 189 |  |

ROMP of hexyl imidonorbornene (HNB)(liquid monomer) using initiators DY6, DY8, and DY9 were investigated by DSC. For initiators DY6 and DY8, ROMP started at around 50° C. and the exotherm peaks maxima were observed at around 86-87° C. For initiator DY9, ROMP started at 80° C. and the exotherm peak maximum was at around 141° C. The DY6 and DY8 gave about the same ΔH (94-116 J/g) in comparison with DY9, which gave the largest ΔH (124 J/g). Initiators DY6 and DY8 posses H$_2$IMes ligand but have Schiff bases containing EDG (OMe) and EWD (NO$_2$) respectively. The fact that initiators DY6 and DY8 show similar characteristics indicate that the presence of EDG or EWD in para position of the benzene ring has no real effect on the ROMP of HNB monomer. The initiator DY9 contains PCy$_3$ ligand and Schiff base with EWG (NO$_2$). The initiators containing PCy$_3$ are generally less reactive than H$_2$IMes containing initiators and therefore DY9 required higher temperature for its activation. The results are summarized in the following table.

|  | Initiator | | | | | | | | |
| --- | --- | --- | --- | --- | --- | --- | --- | --- | --- |
|  | DY6 | | | DY8 | | | DY9 | | |
|  | start | max. | end | start | max. | End | start | max. | end |
| Exotherm temp. (° C.) | 50 | 87 | 110 | 50 | 86 | 125 | 80 | 141 | 170 |
| ΔH (J/g) |  | 94 |  |  | 116 |  |  | 142 |  |

The results indicate that the presence of either EWG or EDG in the para position of the benzene ring has no real effect on the Ru-N bond distances. The Ru-N distances are longer with the H$_2$IMes ligands. The results also show that the ROMP reactivity of the initiators is influenced by the nature of the ligand; i.e. PCy$_3$ or H$_2$IMes. Initiators with H$_2$IMes ligand are shown to be more reactive as is the case with ruthenium 2$^{nd}$ generation initiators.

DSC Studies of ROMP of Norbornene Compounds

The DSC runs were performed following the procedure: the catalyst was weighed into the mixing vessel and dissolved in a minimum of deuterated chloroform (5 drops). The monomer was added and mixed by dual asymmetric centrifuge (DAC) mixer for 5 minutes. After mixing the sample was placed in a vacuum chamber, equipped with an Edwards 5 Vacuum pump, at RT for 30 minutes to ensure all solvent was removed. Approximately 5 mg of the material was pipetted into a standard Perkin-Elmer pan. The open pan was then placed into the TA Instruments Q100 DSC System. Specimens were heated from 25° C. to 300° C. at a rate of 10° C./minute in a nitrogen atmosphere.

A series of polymerisation studies at the monomer to initiator ratio 50:1 were carried out with a selection of liquid norbornene monomers.

Hexyl imidonorbornene (HNB) monomer. The range of catalysts developed give exotherm peaks maxima in the range of 83-143° C. The lowest recorded onset temperature is 50° C. for DNI, but all reactions have initiated by 80° C. The breadth of temperature range spanned by the polymerisation is very catalyst dependent, with some systems showing broad, and others very narrow, polymerisation peaks. Comparison of the actual DSC traces shows that generally initiation of the polymerisation is a "sharp" process, with the temperature range predominantly dictated by the degree of tailing.

Considering the ΔH values associated with the cure peaks, only DN2 has low value on the order of 20 J/g. (These low ΔH values, combined with no evidence of retro-Diels Alder reaction that would indicate the retention of free monomer, is perhaps indicative of early oligomerization, prior to starting the DSC experiment.)

2-Ethylhexyl Imidonorbornene (2-EHNB) Monomer. Similar DSC studies were repeated with an alternative liquid norbornene monomer, 2-EHNB, also using initiators DY10 and DY7, both of which show comparatively high exotherm peaks' maxima (143° C. and 161° C. respectively), with high polymerization onset temperatures, ~120° C. DY7, DY9 and DY10 systems all contain the tricyclohexyl phosphine ligand (PCy$_3$) and differ only in terms of substitution of the benzene ring; incorporating —OMe (EDG), —NO$_2$ (EWG) and —H (no substitution in para position) groups respectively.

DY6 is the H$_2$IMes ligand analogue of DY9 and DY8 is the H$_2$IMes analogue of DY7. The systems bearing the H$_2$IMes ligand in place of the PCy$_3$ ligand show lower polymerisation temperatures, indicating they are more reactive.

DN2 catalyst has low ΔH values associated with the polymerisation reaction. There is also a general trend of decreasing polymerisation temperatures moving from the HNB to the 2-EHNB monomer, assumed to be due to the increased solubility of the catalyst system in the 2-EHNB monomer. In some cases the shift in exotherm temperature is marginal, as in the case of DY5 (86 to 83° C.) and DNI (127 to 119° C.), or extreme, as in the case of DN3 (129 to 70° C.). DY6 and DY8 systems, both containing the H$_2$IMes ligand experience an increase in the exotherm peak maximum associated with the polymerization reaction moving from HNB to 2-EHNB monomer (from 86 to 100° C.).

Decyl imidonorbornene (DecNB) monomer. Increasing the length of the aliphatic side chain still further, experiments (using the initiators DN1, DN2, DN3, DY5, DY8 & DY9) were carried out using the DecNB monomer to determine the extent of variation of polymerization kinetics as a function of monomer selection. DY9 initiator maintains a high reaction temperature for the polymerization of DecNB, even above that reported for the polymerisation of both HNB and 2-EHNB monomers. The reaction onset was observed at 140° C., with the exotherm peaks' maxima at 199° C. The polymerization process was completed by 225° C. and showed an associated ΔH value of −71 J/g. DY9 initiator contains a tricyclohexyl phosphine ligand (PCy$_3$) but otherwise is the analogue of the DY8 system. For the polymerization of DecNB, the DY8 system showed the onset of polymerisation by 50° C., with the exotherm peaks maxima recorded at 107°

C. The polymerization process was completed by 175° C. and showed an associated ΔH value of −147 J/g.

5-Ethylidene, 2-norbornene (5E2NB) monomer. The reactivity of the DN1, DN2, DN3, DY5 and DY8 initiators were compared using 5E2NB monomer. In the DN initiator series, there was a rise in the temperature of the exotherm peaks maxima. This monomer is extremely volatile with a boiling point of 146° C., which explains the lower associated ΔH values obtained with DN1 initiator, the highest temperature system. In contrast the DY series of initiators appear to show much more reproducible reaction temperatures across the range of different monomers used.

Initiators DRY11 to DRY13

The initiators DRY11 and DRY13 contain IMesH2 ligands and a 5-membered chelation ring, with —NO$_2$ (EWG) and —OMe (EDG), respectively, in the meta position of the benzene ring attached to the nitrogen. The initiator DRY12 contains IMesH2 ligand and a 5-membered chelation ring, with —OMe (EDG) in the ortho position of the benzene ring attached to the nitrogen. Initiators DRY11-DRY13 were characterised by $^1$HNMR and $^{13}$CNMR. The structures of the Initiators DRY11-DRY13 have been confirmed by X-Ray Crystallography. The initiators were dissolved in CDCl$_3$, kept at 50° C. and $^1$H NMR spectra were taken at different intervals over the period of up to 24 h and were shown to be stable.

Romp Reactions by NMR

The results of HNMR studies of ROMP reactions of DMENB (dimethylester norbornene) and 2-EHNB with Durham initiators DRY 11, DRY12 and DRY13 are summarised in the table below.

| Reaction time, (hours) | 2-EHNB | | | DMENB | | |
|---|---|---|---|---|---|---|
| | DRY 11 m-NO2 % Conv | DRY 12 o-OMe % Conv | DRY 13 m-OMe % Conv | DRY 11 m-NO2 % Conv | DRY 12 o-OMe % Conv | DRY 13 m-OMe % Conv |
| 2 | 47 | 3 | 14 | 14 | — | 3 |
| 4 | 62 | 5 | 28 | — | 2 | — |
| 7 | — | — | — | 30 | 4 | 9 |
| 8 | 80 | — | 50 | — | — | — |
| 30 | 90 | 20 | 82 | 52 | 8 | 23 |
| 54 | 97 | — | 90 | 63 | — | 42 |

The comparison of the monomer to polymer conversion with time for the ROMP reactions using DRY11 and DRY13 is very interesting. The presence in meta position of NO$_2$ group (EWG) in meta position in DRY11 weakens and OMe group (EDG) strengthens the chelation as expected. The comparison of the monomer to polymer conversion with time for the ROMP reactions using DRY12 and DRY13 is also very interesting. The effect of OMe group (EDG) in ortho position (DRY12) is more pronounced in comparison with that in meta position (DRY13); the chelation is stronger and hence more energy is required to break it and hence lower reactivity at room temperature Romp Reactions by DSC ROMP of 2-EHNB using Durham initiators DRY11, DRY12 and DRY13 were investigated by DSC. The results are summarized in the table below.

| | Initiator | | | | | | | | |
|---|---|---|---|---|---|---|---|---|---|
| | DRY11 (m-NO$_2$) | | | DRY12 (o-OMe) | | | DRY13 (m-OMe) | | |
| | start | max | end | start | max | end | start | max | end |
| Exotherm temp. (° C.) | 45 | 75 | 138 | 55 | 95 | 160 | 40 | 78 | 153 |
| ΔH (J/g) | | 87 | | | — | | | 149 | |

ROMP of DMENB monomer using Durham initiators DRY11, DRY12 and DRY13 were investigated by DSC. The results are shown in the Table below.

| | Initiator | | | | | | | | |
|---|---|---|---|---|---|---|---|---|---|
| | DRY 11 (m-NO$_2$) | | | DRY 12 (o-OMe) | | | DRY 13 (m-OMe) | | |
| | start | max | end | start | max | end | start | max | end |
| Exotherm temp. (° C.) | 20 | 70 | 140 | 30 | 75 | 165 | 40 | 80 | 165 |
| ΔH (J/g) | | 140 | | | 140 | | | 123 | |

The results indicate only small differences in the exotherm peak maxima for the ROMP of the two monomers with initiators DRY11-DRY13. It indicates that the presence of EWG or EDG in meta and also the presence of EDG in meta or ortho position of the benzene ring attached to the nitrogen has no real effect on the ROMP reactions.

Synthesis of Durham Initiators DRY11 and DRY13

These initiators have a five member ring chelation in common but with NO$_2$ (electron withdrawing) and —OMe (electron donating) groups in ortho and meta positions.

DRY 11: R = NO$_2$
DRY 13: R = OMe

DRY 12

These initiators are made via two steps: step 1, synthesis of the Schiff base ligands L11-L13 and step 2, reaction of the Schiff base ligands with pyridine modified second generation ruthenium (VIII) to prepare DRY11-DRY13.

COMPARATIVE DATA FOR COMMERCIALLY AVAILABLE CATALYSTS

Comparative Example 1

Two Initiators from Ciba Corporation, one containing nitrogen and one containing sulphur, were tested for their activity level at room temperature in the ROMP of endo, exo-dimethoxydicarboxylate norbornene monomer. The nitrogen containing initiator gave complete conversion of the monomer in 50 hours at room temperature; the sulphur containing initiator gave complete conversion in 25 hours at room temperature.

Comparative Example 2

Two S-containing initiators were used in the ROMP of dicyclopentadiene (DCPD): the Ciba initiator as shown in Comparative Example 1 with an unsubstituted benzene ring, and an S-containing initiator of the same structure except with a $CH_3$ in the para position on the benzene ring. Both polymerised DCPD at 60° C. For the CSY initiator, the polymerisation started at 30° C. and showed a maximum exotherm peak at about 200° C. For the initiator with $CH_3$ in the para position on the benzene ring, the polymerisation started at 30° C. and showed a maximum exotherm peak at about 180° C.

Comparative Example 3

Three N-containing initiators were used in the ROMP of dicyclopentadiene (DCPD): the CNY initiator as shown in Comparative Example 1 with an unsubstituted benzene ring, a N-containing initiator of the same structure except with $CH_3$ in the ortho position on the benzene ring, and a N-containing initiator of the same structure with $CH_3$ in the ortho and the para position on the benzene ring. The CNY initiator with the unsubstituted benzene ring was inactive for the polymerisation of DCPD even at elevated temperatures. The N-containing initiator with $CH_3$ in the ortho position on the benzene ring polymerised DCPD at 60° C. and showed a maximum exotherm peak at about 170° C. The N-containing initiator with $CH_3$ in both the ortho and the para position on the benzene ring polymerized DCPD at 60° C. and showed a maximum exotherm peak at about 180° C.

Comparative Example 4

The ROMP of hexyl imido-norbornene (HNB) (liquid monomer) using the CNY initiator was investigated by DSC: polymerization started at about 40° C. with an exotherm maximum at around 55° C.

Comparative Example 5

The ROMP of endo, exo-dimethyl ester norbornene using the CNY initiator was performed at 5° C. The monomer to polymer conversion after 24 hours was 9%; after 48 hours, was 25%; after 72 hours was 40%, and after 120 hours, was 73%.

Comparative Example 6

The CNY initiator was used in the homo-polymerisation of other norbornene monomers. Different polymerization rates were obtained for different monomers with the Tg controlling monomers giving the highest rates. The monomers and their conversion rates are presented in the following table.

| MONOMER | CONVERSION RATE IN HOURS AT ROOM TEMPERATURE |
|---|---|
| Dimethoxycarboxylate norbornene | 10% in 5 hours |
| | 65% in 24 hours |
| | 90% in 48 hours |
| Styrene-imido norbornene | 3% in 5 minutes |
| | 12% in 1 hours |
| | 22% in 5 hours |
| | 38% in 24 hours |
| Phenyl-imido norbornene | 50% in 1 hour |
| | 90% in 5 hours |
| | 90% in 24 hours |
| | 90% in 48 hours |
| Th-imido norbornene | 8% in 24 hours |
| | 20% in 48 hours |

In general, the design of the ligands on the inventive initiators is based on the incorporation of a deactivating group (—C6F4) and an anchor group (—COOMe). The deactivating group because of its electron withdrawing nature makes the nitrogen-Ruthenium chelating stronger and therefore less reactive at room temperature. The anchor group provides the means for supporting the initiator on a support.

General Description of Initiators DY1 to DY4

The two chlorine ligands in CIBA initiator are replaced with Ligand (9) to obtain initiator DY1.

The two chlorine ligands in Grubbs modified $2^{nd}$ generation initiator are replaced with Ligand (9) to obtain initiator DY2. The two chlorine ligands in CIBA initiator are replaced with Ligand (9) and the $^iPr_3$ ligand is replaced with $PCy_3$ ligand to obtain initiator DY3. The two chlorine ligands in CIBA initiator are replaced with Ligand (9) and the $^iPr_3$ ligand is replaced with IMesH2 ligand to obtain Initiator DY4. Two synthetic routes are possible. Route 1: Ruthenium second generation (II) is modified with pyridine to prepare modified ruthenium second generation (VIII). The reaction of VIII with the prepared ligand 10 gives ruthenium initiator (IX) which is then reacted with the Ligand 9 to obtain DY4. Route 2: Ruthenium second generation (II) is reacted with the prepared ligand 10 to give ruthenium initiator (IX) which is then reacted with Ligand 9 to obtain DY4.

General Description of DN1 to DN4

It was anticipated that the reactivity of initiators can be modified by incorporating either electron withdrawing groups (EWG) or electron donating groups (EDG) in the para position on the benzene ring connected to nitrogen. The incorporation of EWG or EDG was predicted to weaken or strengthen the chelation bond respectively and therefore influence the ROMP behaviour of the resulting initiators.

DN1-DN3 all have a 6-membered chelation ring and contain functional groups such as —OCH$_3$ (good EDG), —CH$_3$ (weak EDG) and NO$_2$ (good EWG), respectively, in the para position of the benzene ring attached to the nitrogen. Slugovc initiator (with no functional groups on the benzene ring) was prepared for comparison and is referred to as S5, having the structure:

General Description of DY6 to DY10

The initiators DY6-DY10 all have a 5-membered chelation ring and contain functional groups:—OCH$_3$ (good EDG), —CH$_3$ (weak EDG) and NO$_2$ (good EWG), respectively, in para position of the benzene ring attached to the nitrogen. Initiators DY6 and DY8 both contain IMesH2 ligand and OMe (EDG) and NO$_2$ (EWG), respectively, in para position of the benzene ring attached to nitrogen. Initiators DY7 and DY9 both contain PCy$_3$ ligand and OMe (EDG) and NO$_2$ (EWG), respectively, in para position of the benzene ring attached to nitrogen. Initiators DY10 contain PCy$_3$ ligand and no substitution in para position of the benzene ring attached to nitrogen. Initiators DY6-DY10 were characterised by $^1$HNMR and $^{13}$CNMR. The structures of the Initiators DY6 and DY7 have been confirmed by X-Ray Crystallography. The initiators were dissolved in CDCl$_3$, kept at 50° C. and $^1$H NMR spectra were taken at different intervals over the period of up to 24 hours and were shown to be stable.

What is claimed:

1. A ruthenium initiator for the ring-opening metathesis polymerization of cyclic olefins, the initiator having a structure selected from the group consisting of:

DY1

DY3

DY4

2. A ruthenium initiator for the ring-opening metathesis polymerization of cyclic olefins, the initiator having the structure:

DY2

3. A polymer resulting from the ring opening metathesis of dicyclic olefins in the presence of one or more of the initiators of any one or more initiators of claim 1, in which the dicyclic olefins contain functionality additional to the olefinic double bonds, and in which the resultant polymer contains olefinic double bonds and the additional functionality.

4. A polymer resulting from the ring opening metathesis of dicyclic olefins in the presence of the initiator of claim 2, in which the dicyclic olefins contain functionality additional to the olefinic double bonds, and in which the resultant polymer contains olefinic double bonds and the additional functionality.

* * * * *